US009463050B2

(12) United States Patent
Schwend

(10) Patent No.: US 9,463,050 B2
(45) Date of Patent: Oct. 11, 2016

(54) SLIDING ROD SYSTEM FOR CORRECTING SPINAL DEFORMITIES

(75) Inventor: Richard M Schwend, Kansas City, MO (US)

(73) Assignee: The Children's Mercy Hospital, Kansas City, MO (US)

( * ) Notice: Subject to any disclaimer, the term of this patent is extended or adjusted under 35 U.S.C. 154(b) by 466 days.

(21) Appl. No.: 13/000,869

(22) PCT Filed: Aug. 7, 2009

(86) PCT No.: PCT/US2009/053145
§ 371 (c)(1), (2), (4) Date: Mar. 21, 2011

(87) PCT Pub. No.: WO2010/017471
PCT Pub. Date: Feb. 11, 2010

(65) Prior Publication Data

US 2011/0184463 A1 Jul. 28, 2011

Related U.S. Application Data

(60) Provisional application No. 61/086,853, filed on Aug. 7, 2008, provisional application No. 61/155,276, filed on Feb. 25, 2009.

(51) Int. Cl.
*A61B 17/70* (2006.01)
*A61B 17/00* (2006.01)

(52) U.S. Cl.
CPC .... *A61B 17/705* (2013.01); *A61B 2017/00867* (2013.01)

(58) Field of Classification Search
CPC .......... A61B 17/7049; A61B 17/7056; A61B 17/7019
USPC .......................... 606/246–279, 75, 324, 330
See application file for complete search history.

(56) References Cited

U.S. PATENT DOCUMENTS

| | | | | |
|---|---|---|---|---|
| 5,102,412 | A * | 4/1992 | Rogozinski | 606/86 A |
| 5,133,717 | A * | 7/1992 | Chopin | A61B 17/7055 606/264 |
| 5,261,907 | A * | 11/1993 | Vignaud et al. | 606/60 |
| 5,540,689 | A * | 7/1996 | Sanders | A61B 17/7032 24/531 |

(Continued)

FOREIGN PATENT DOCUMENTS

WO 2007045892 A1 4/2007

*Primary Examiner* — Eduardo C Robert
*Assistant Examiner* — Michelle C Eckman
(74) *Attorney, Agent, or Firm* — Tracey S. Truitt; Polsinelli PC.

(57) ABSTRACT

A sliding rod system for correcting a spinal deformity is disclosed. The sliding rod system may include at least one elongated thoracic sliding rod for slidable engagement with a plurality of connectors with each connector being fixedly engaged to multiple ribs of a patient for applying a continuous corrective force to the spinal column. Each of the connectors has a connector body that defines an upper clamp portion in communication with a lower clamp portion. The upper clamp is in slidable engagement with the at least one elongated thoracic sliding rod and the lower clamp is in fixed engagement with a respective rib of a patient. As the patient grows, the thoracic sliding rod slides relative to each connector, thereby permitting the sliding rod system to accommodate the gradual separation of the ribs during patient growth while providing continued corrective pressure to the patient's spinal column.

11 Claims, 24 Drawing Sheets

(56) References Cited

U.S. PATENT DOCUMENTS

| | | | | |
|---|---|---|---|---|
| 5,586,983 | A * | 12/1996 | Sanders et al. | 606/277 |
| 5,620,444 | A | 4/1997 | Assaker | |
| 5,800,434 | A * | 9/1998 | Campbell, Jr. | 606/279 |
| 6,136,000 | A * | 10/2000 | Louis et al. | 606/250 |
| 6,368,320 | B1 * | 4/2002 | Le Couedic et al. | 606/250 |
| 6,524,311 | B2 * | 2/2003 | Gaines, Jr. | 606/278 |
| 7,029,472 | B1 * | 4/2006 | Fortin | 606/60 |
| 7,628,799 | B2 * | 12/2009 | Richelsoph et al. | 606/250 |
| 2003/0144665 | A1 * | 7/2003 | Munting | 606/61 |
| 2004/0106921 | A1 * | 6/2004 | Cheung | A61B 17/7001 606/250 |
| 2004/0162558 | A1 * | 8/2004 | Hegde et al. | 606/61 |
| 2006/0217718 | A1 * | 9/2006 | Chervitz et al. | 606/61 |
| 2007/0049932 | A1 * | 3/2007 | Richelsoph et al. | 606/61 |
| 2007/0149909 | A1 * | 6/2007 | Fortin et al. | 602/32 |
| 2007/0270805 | A1 * | 11/2007 | Miller et al. | 606/61 |
| 2007/0270817 | A1 * | 11/2007 | Rezach | 606/61 |
| 2008/0262553 | A1 * | 10/2008 | Hawkins et al. | 606/278 |

* cited by examiner

SLIDING ROD SYSTEM FOR CORRECTING SPINAL DEFORMITIES

RELATED APPLICATIONS

This application is filed under 35 USC §371 from PCT Patent Application No. PCT/US2009/053145, which claims priority of a previously filed and U.S. provisional patent application Ser. No. 61/155,276, filed Feb. 25, 2009, and U.S. provisional patent application Ser. No. 61/086,853, filed Aug. 7, 2008. The identified previously filed applications are hereby incorporated by reference into the present application.

FIELD

The present document relates to a system and related method for treating skeletal deformities, and in particular to a system and related method for the correction of spinal deformities that does not require planned subsequent surgical intervention after initial implantation into a patient.

BACKGROUND

Spinal deformities and the challenge of correcting spinal deformities in young children are well known. Such deformities may include, but are not limited to, infantile scoliosis, neuromuscular scoliosis requiring fixation to the pelvis, spinal deformities with associated kyphosis, thoracic insufficiency syndrome with fused ribs requiring thoracostomy, and syndrome-related scoliosis. Various systems have been used in the past to treat pediatric patients suffering from spinal deformities such as the use of braces and casting, while other types of systems for treating spinal deformities include traditional spine implant systems and growth rods. These types of prior art systems and devices often have limited fixation points and may depend on periodic adjustment for systems that utilize growth rods in order to accommodate the natural spine growth of a pediatric patient. As such, this periodic lengthening and adjustment requires surgical intervention every time the device is required to be lengthened, thus putting additional strain on the young patient. A recent development in the field, the VEPTR technique, is considered an advancement in the field of correcting spinal deformities in pediatric patients, but utilizes an arrangement of growth rods that has limited fixation points along the spine and still requires subsequent surgical intervention for periodic adjustment of the growth rods as the pediatric patient grows over time. Furthermore, pediatric patients may be very small in stature and have thin posterior tissue, thus creating the necessity for a low profile system that corrects skeletal deformities using numerous and/or movable fixation points.

Accordingly, there remains a need in the art for a system and related method for a correcting a spinal deformity that does not require subsequent growth-related surgical intervention after the initial implantation of the system into a patient.

SUMMARY

In one embodiment, a sliding rod system for correcting a spinal deformity in a pediatric patient may include at least one thoracic sliding rod in slidable engagement with at least one connector with at least one connector having a connector body that includes an upper clamp portion transversely positioned relative to a lower clamp portion. The upper clamp portion may include upper clamp arms that define an upper conduit to slidably engage at least one thoracic sliding rod when in a closed position. The lower clamp portion includes lower clamp arms defining a lower clamp conduit to fixedly engage a respective rib of a patient, wherein at least one thoracic sliding rod applies a continuous corrective force to a spinal column of the patient through the fixed engagement of at least one thoracic sliding rod with each respective rib of the patient as at least one thoracic sliding rod is in slidable engagement with at least one connector.

In another embodiment, a sliding rod system may include a pair of thoracic sliding rods with one of the pair of thoracic sliding rods being slidably engaged to a plurality of connectors engaged to one or more ribs along one side of a patient's rib cage. The other one of the pair of thoracic sliding rods may be slidably engaged to another plurality of connectors engaged to another one or more ribs along the other side of the patient's rib cage such that a continuous corrective force is applied to the patient's spinal column by the pair of thoracic sliding rods. The plurality of connectors each have a connector body that includes an upper clamp portion transversely positioned relative to a lower clamp portion with the upper clamp portion including opposed upper clamp arms that collectively define an upper clamp conduit slidably engaged a respective one of the pair of thoracic sliding rods. The lower clamp portion includes opposing lower clamp arms that collectively define a lower conduit fixedly engaged to a skeletal structure of the patient. The connector body may be made from a shape-memory alloy that permits the connector body to have an open position at a first temperature range while permitting the connector body to assume a closed position when the connector body is exposed to warmer second temperature range such that the upper clamp portion of the connector body is slidably engaged with one of the pair of thoracic sliding rods and the lower clamp portion is fixedly engaged to the patient's skeletal area.

In a further embodiment, a sliding rod system may include a pair of thoracic sliding rods being slidably engaged to a plurality of connectors, which are engaged to one or more ribs along one side of a patient's rib cage. Another pair of thoracic sliding rods are slidably engaged to another plurality of connectors engaged to another one or more ribs along the other side of the patient's rib cage such that a continuous corrective force is applied to the patient's spinal column by each pair of thoracic sliding rods. Each of the plurality of connectors includes a connector body that having a pair of upper clamp portions transversely positioned relative to a lower clamp portion with each of the upper clamp portions defining a pair of upper clamp arms that collectively define a respective upper conduit. The upper clamp conduit is slidably engaged to a respective one of the pair of thoracic sliding rods. The lower clamp portion includes opposing lower clamp arms that collectively define a lower conduit that is fixedly engaged to a skeletal structure of the patient. The connector body is made from a shape-memory alloy that permits each pair of upper clamp arms and the lower clamp arms of the connector body to have an open position at a first temperature range, while permitting each pair of upper clamp arms and the lower clamp arms of the connector body to assume a closed position when exposed to a second temperature range that is warmer than the first temperature range such that at least one of the pair of upper clamp portions is slidably engaged with one of the pair of thoracic sliding rods and the lower clamp portion is fixedly engaged to the patient's skeletal area.

In yet another embodiment, a method for correcting a spinal deformity in a patient may include:

a) providing a sliding rod system comprising at least one thoracic sliding rod for slidable engagement with a plurality of connectors with each of the plurality of connectors having a connector body that includes an upper clamp portion transversely positioned relative to a lower clamp portion. The upper clamp portion includes a pair of upper clamp arms that collectively define an upper clamp conduit to engage at least one thoracic sliding rod. The lower clamp portion includes a pair of opposing lower clamp arms that collectively define a lower clamp conduit, wherein each connector body is made from a shape-memory alloy that permits the connector body to have an open position at a first temperature range, while permitting the connector body to assume a closed position when exposed to a second temperature range that is warmer than the first temperature range;

b) surgically accessing a plurality of ribs of the patient and engaging at least one of the plurality of ribs to a respective connector such that each one the plurality of ribs engaged to a respective connector is disposed between the lower clamp arms of the respective connector in an open position, wherein the respective connector is exposed to a first temperature range;

c) inserting at least one thoracic sliding rod through a respective connector such that at least one thoracic sliding rod is disposed between the upper clamp arms of the respective one of the plurality of connectors in the open position, wherein the respective connector is exposed to the first temperature range; and d) allowing each of the plurality of connectors to assume the closed position when exposed to the second temperature range that is warmer than the first temperature range after engagement of the respective one of the plurality of connectors to at least one thoracic sliding rod and at least one of the plurality of ribs, wherein at least one thoracic sliding rod applies a continuous corrective force to a spinal column of a patient.

In a further embodiment, the sliding rod system may include a lumbar rod component that anchors the lower portion of a pair of thoracic sliding rods to the lumbar area of the patient. The lumbar rod component includes a pair of rod-rod connectors adapted to engage a respective thoracic sliding rod to a respective lumbar sliding rod. In addition, each of the rod-rod connectors defines a pair of inverted conduits with one of the inverted conduits being in a slidable engagement with the thoracic sliding rod while the other one of the inverted conduits is in a slidable engagement with the lumbar sliding rod.

Additional objectives, advantages and novel features will be set forth in the description which follows or will become apparent to those skilled in the art upon examination of the drawings and detailed description which follows.

BRIEF DESCRIPTION OF THE DRAWINGS

Corresponding reference characters indicate corresponding elements among the view of the drawings. The headings used in the figures should not be interpreted to limit the scope of the claims.

DETAILED DESCRIPTION

Figure 1:
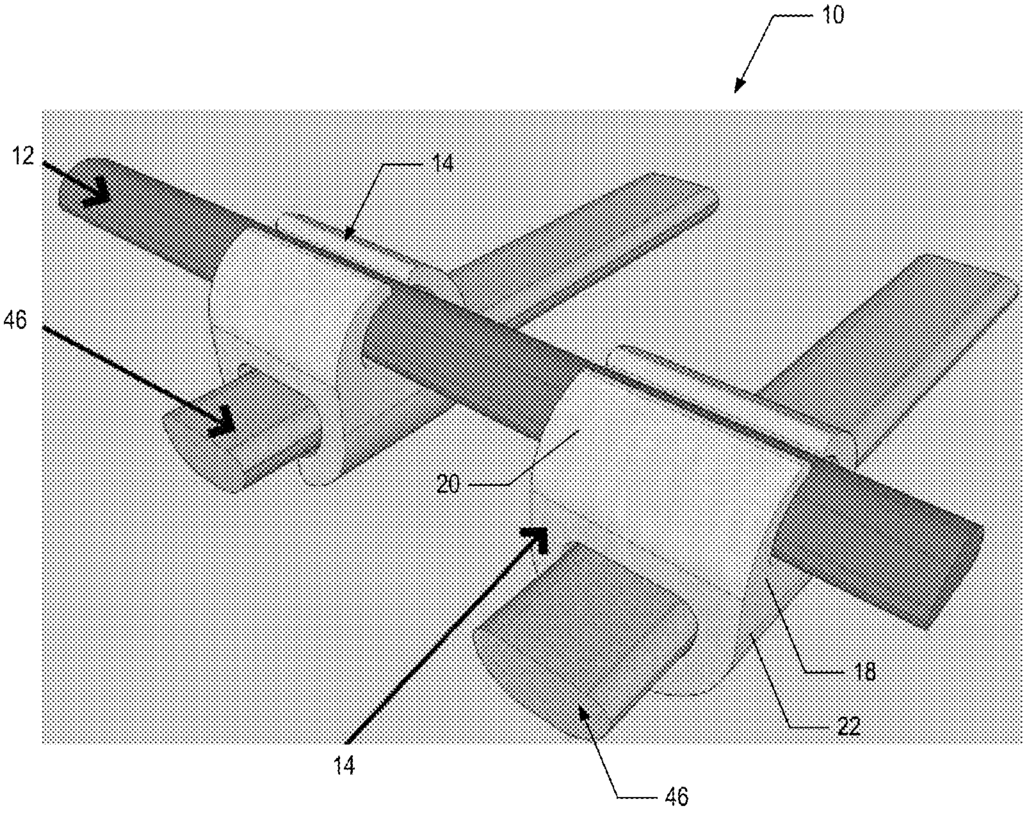
FIG. 1 is a simplified illustration of a single rod embodiment for the sliding rod system showing connectors that engage a respective rib to an thoracic sliding rod.
Figure 2:
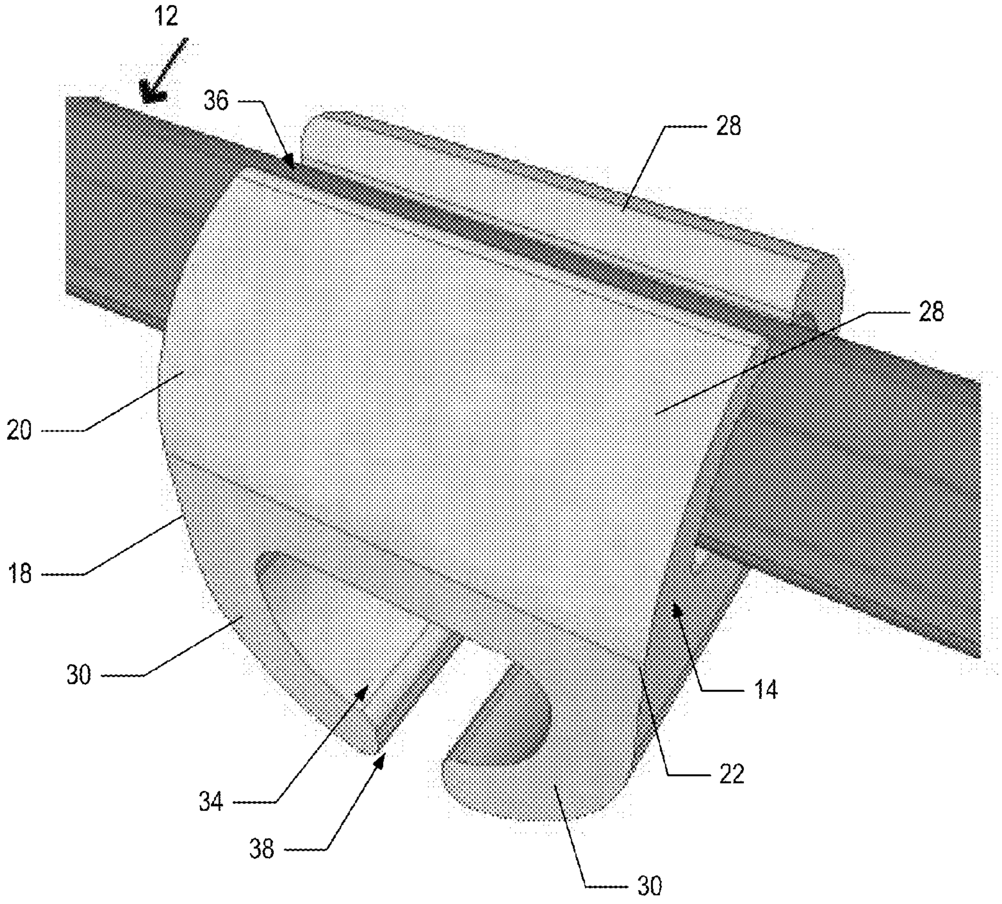
FIG. 2 is an enlarged perspective view showing the connector slidably engaged to the thoracic sliding rod of the sliding rod system.
Figure 3:
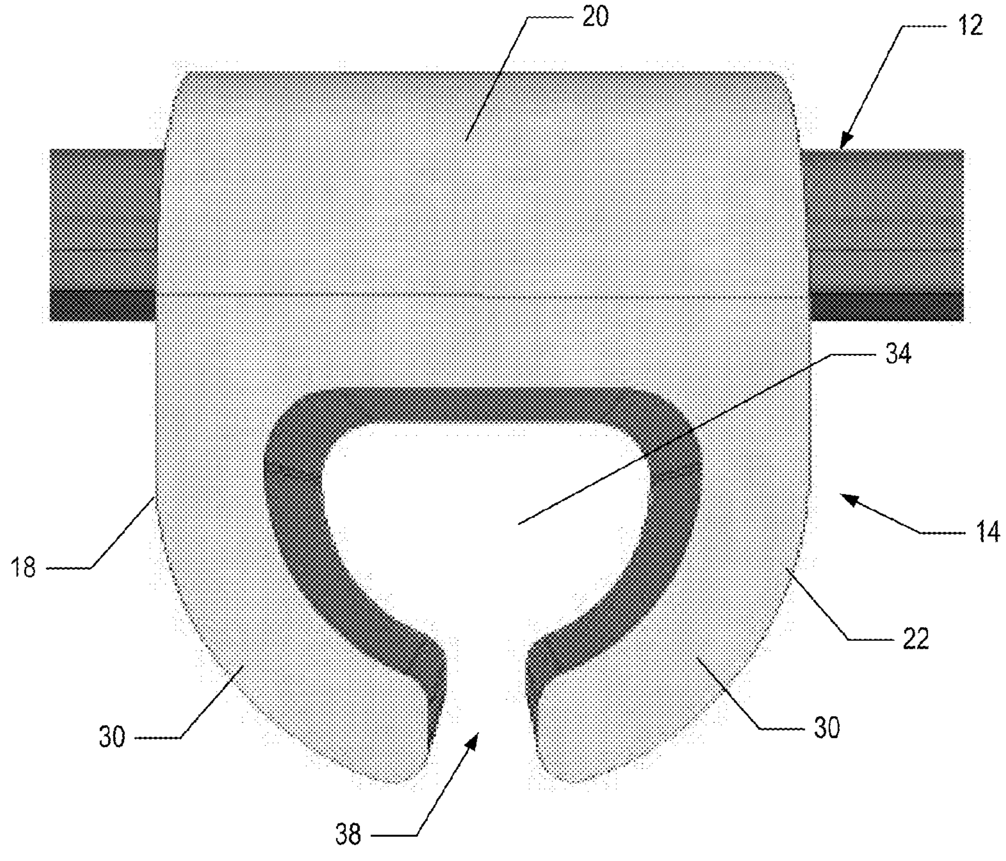
FIG. 3 is an enlarged side view of the sliding rod system showing the connector in the closed position.
Figure 4:
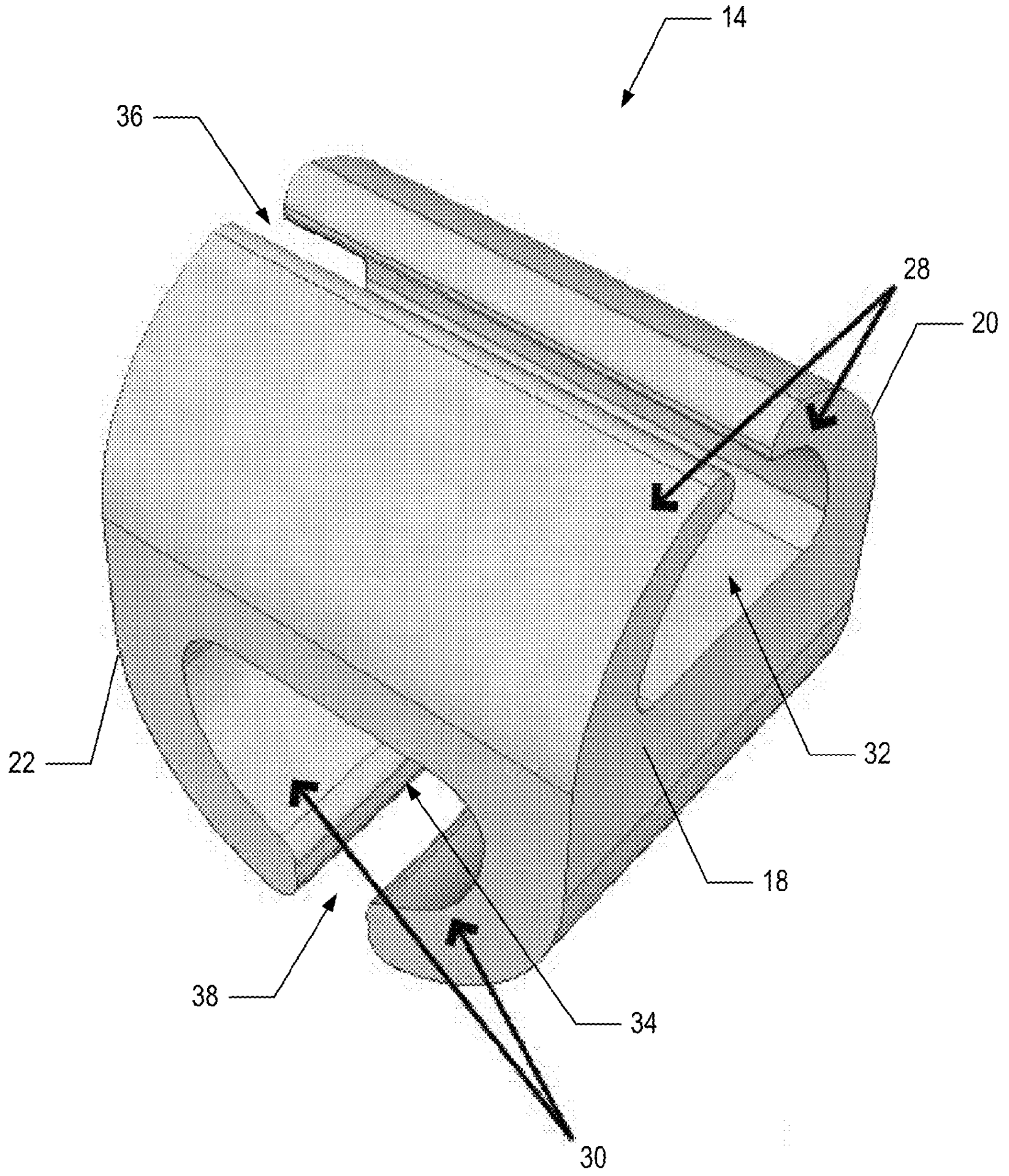
FIG. 4 is an elevated perspective view of the connector showing the upper and lower clamp portions of the connector in the closed position.
Figure 5:
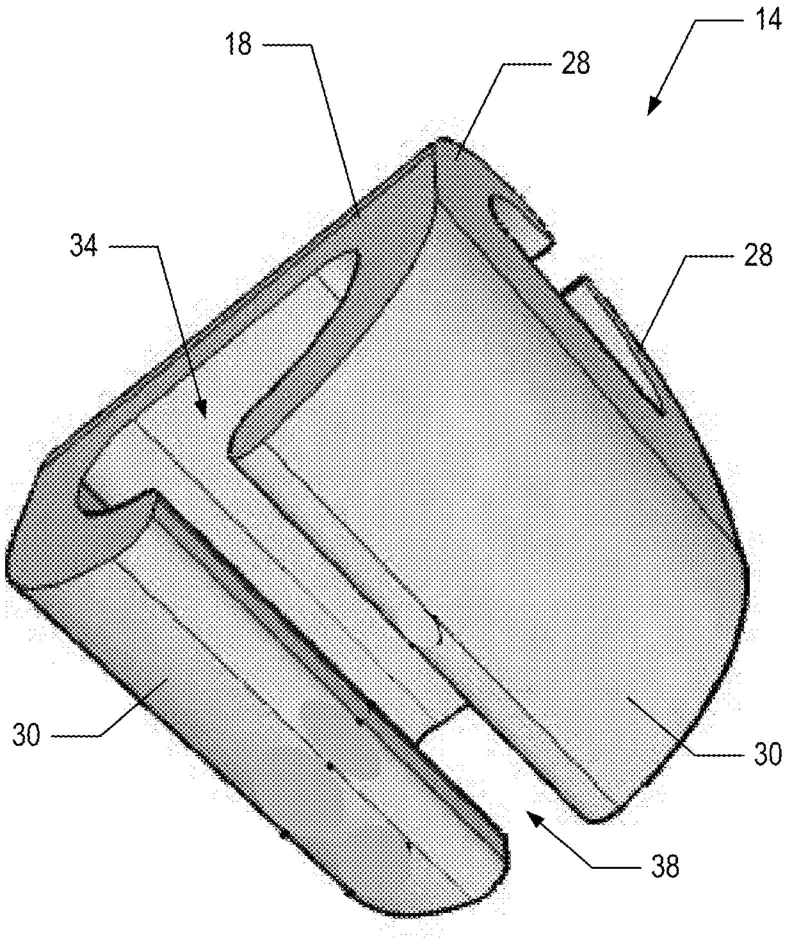
FIG. 5 is another perspective view of the connector of FIG. 4 showing the upper and lower clamp portions of the connector in the closed position.
Figure 6:
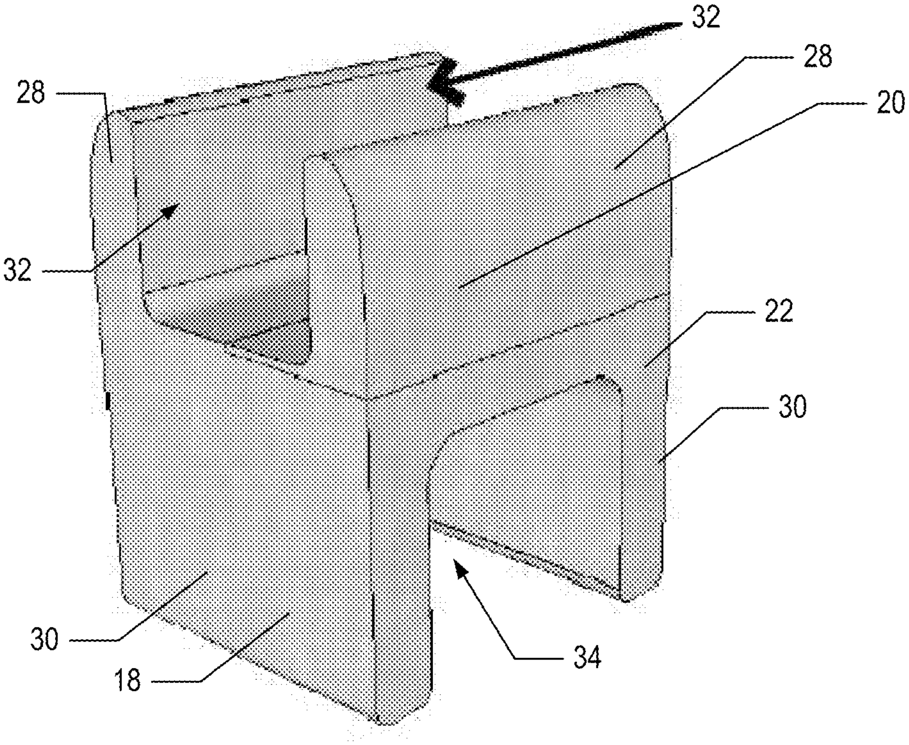
FIG. 6 is a perspective view of the connector showing the upper and lower clamp portions of the connector both in the open position.
Figure 17:
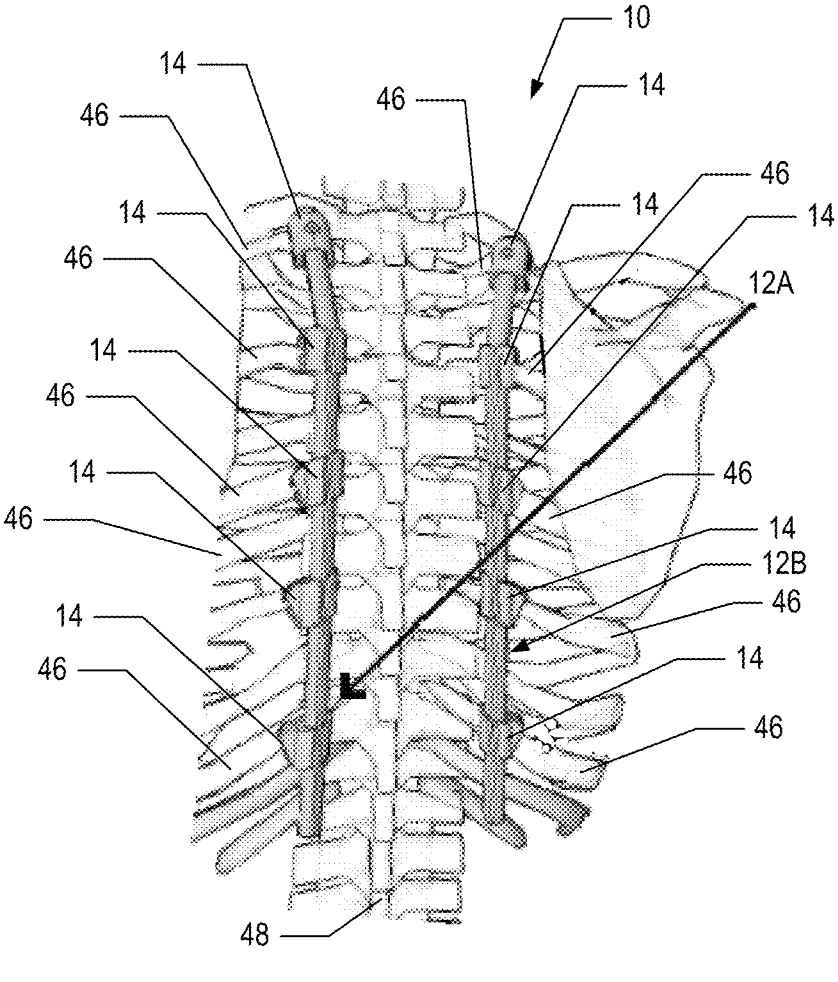
FIG. 17 is an illustration showing the single rod embodiment of the sliding rod system surgically implanted to both sides of a patient's rib cage.

Referring to the drawings, embodiments of a sliding rod system for correcting spinal deformities are illustrated and generally indicated as 10, 10A or 10B in FIGS. 1-34. In a single rod embodiment of the sliding rod system generally indicated as 10 in FIG. 1, the sliding rod system 10 may include a thoracic sliding rod 12 adapted for insertion into one or more connectors 14 for engagement of the thoracic sliding rod 12 to a plurality of ribs 46 along one side of the patient's rib cage. As shown in FIG. 17, the sliding rod system 10 may include a pair of thoracic sliding rods 12A and 12B with each sliding rod 12 being positioned approximately parallel to the spinal column 48 of a patient. As such, when each of the thoracic sliding rods 12A and 12B are inserted through a series of connectors 14, each thoracic sliding rod 12 applies a continuous corrective force upon patient's spinal column 48 through the engagement of the sliding rods 12A and 12B with the ribs 46 on both sides of the pediatric patient's rib cage that maintains the correction of the spinal deformity and allows the pediatric chest and spine of a patient to continue to grow in all directions, without any surgical intervention after implantation.

Figure 11:
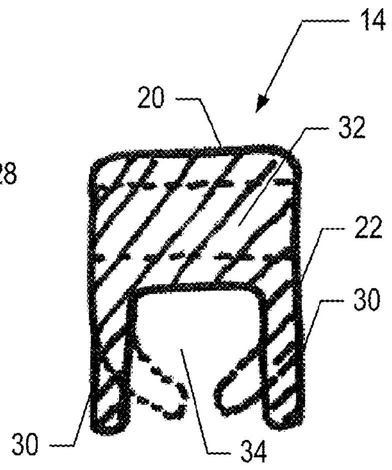
FIG. 11 is another cross-sectional view of the connector showing the arms of the lower clamp portion in the open position (solid) and the closed position (phantom)

Referring to FIGS. 1-4, one embodiment of connector 14 has a connector body 18 that defines an upper clamp portion 20 adapted to slidably engage the thoracic sliding rod 12 and a lower clamp portion 22 adapted to fixedly engage a rib 46. As used herein the language "slidably engage" or "slidable engagement" shall mean that the thoracic sliding rod 12 is in physical contact with the upper clamp portion 20 of the connector 14 and that the connector 14 may move or slide relative to the thoracic sliding rod 12 as the connector moves over time as the ribs 46 grow farther apart from each other as the pediatric patient grows over time, thereby causing a greater separation between respective connectors 14 fixedly engaged to each respective rib 46. In addition, as used herein, the language "fixedly engage" and "fixed engagement" shall mean that the rib 46 is in physical contact with the lower clamp portion 20 and that the connector 14 does not move relative to the thoracic sliding rod 12 as the ribs 46 grow farther apart. As further shown, the upper clamp portion 20 defines a pair of upper clamp arms 28 that slidably along engage along the thoracic sliding rod 12 when in the closed position, while the lower clamp portion 22 defines a pair of lower clamp arms 30 adapted to fixedly engage a respective rib 46 when also in the closed position. In one embodiment, the connector 14 may be made from a shape-memory alloy, such as Nitinol (NiTi), that permits the upper and lower clamp arms 28 and 30 to be in an open position (shown in phantom) at a first temperature range while assuming a closed position at a second temperature range that is warmer than the first temperature range. When the connector 14 is exposed to a temperature in the second temperature range, such as the body temperature of the patient after implantation of the sliding rod system 10, the shape-memory alloy of the connector 14 causes the lower and upper clamp arms 28 and 30 to bend to the closed position and engage the thoracic sliding rod 12 and ribs 46. As such, both the upper clamp arms 28 and lower clamp arms 30 are adapted to be bent from an open position (FIG. 6) when at ambient temperature or colder to a closed position (FIG. 5) when exposed to a higher temperature, such as when the connector 14 is heated by the core body temperature of the patient. In the closed position, the upper clamp arms 28 of connector 14 form an upper conduit 32 that defines an upper channel 36 between arms 28 that permits the thoracic sliding rod 12 to engageably slide along the longitudinal axis of rod 12 relative to the connector 14, while the lower clamp arms 30, oriented transversely to the upper clamp portion 20, form a lower conduit 34 that defines a lower channel 38 between arms 30 adapted to fixedly engage a respective rib 46 when the lower clamp portion 22 of the connector 14 is placed in the closed position. Referring to FIG. 11, this sequence of the lower clamp arms 30 being bent from the open position (shown in solid) to the closed position (shown in phantom) is illustrated.

Figure 7A:
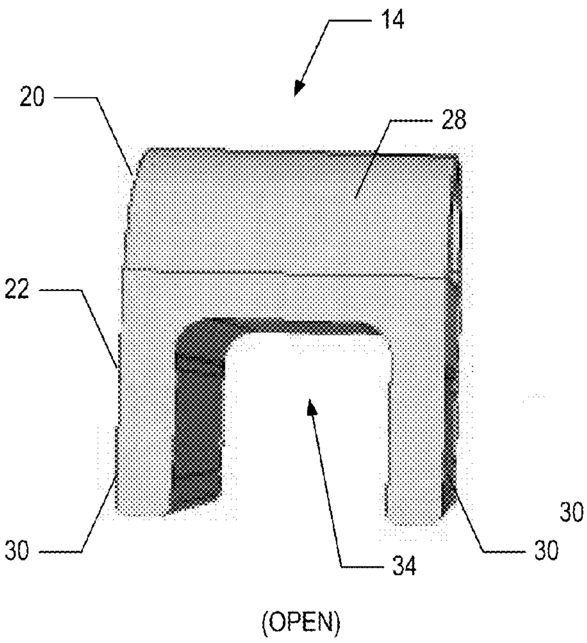
FIGS. 7A and 7B illustrate the open and closed positions of the lower clamp portion of the connector.
Figure 7B:
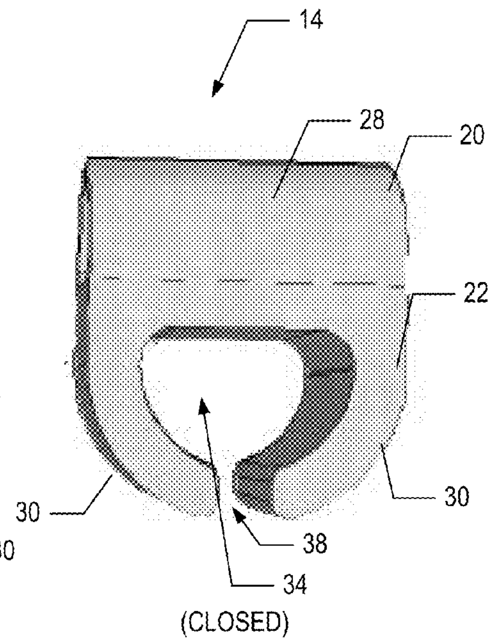
Figures 8A, 8B:
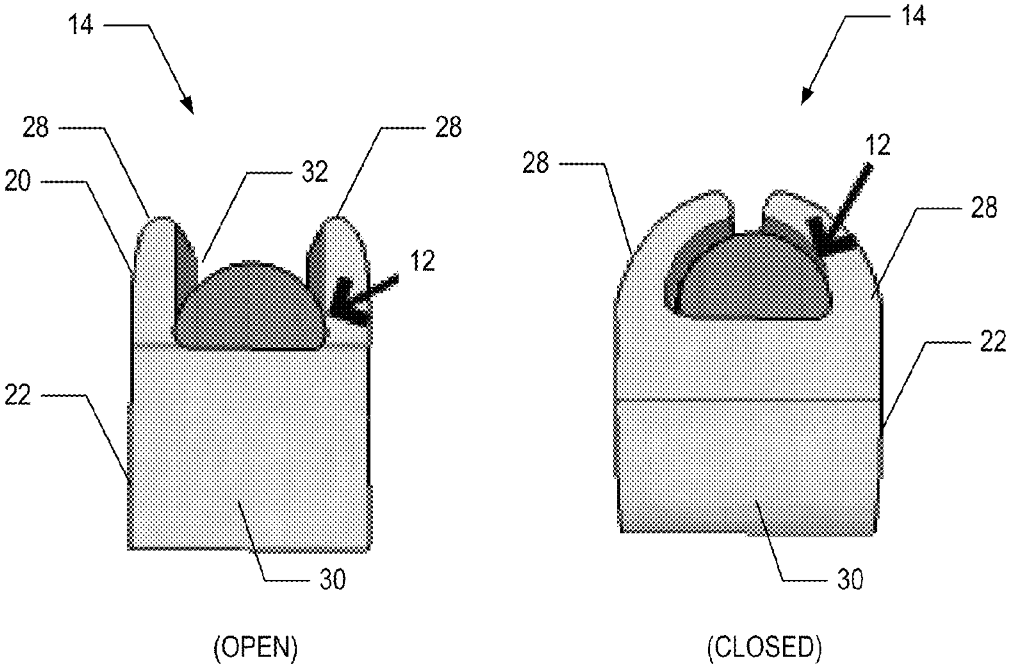
FIGS. 8A and 8B illustrate the open and closed positions of the upper clamp portion of the connector relative to the rod.
Figure 9:
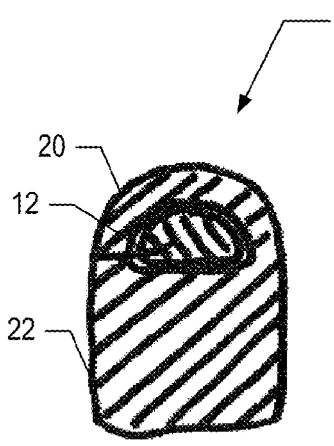
FIG. 9 is a cross-sectional view of an embodiment of the connector having a fully closed upper clamp portion adapted to anchor the thoracic sliding rod.
Figure 10:
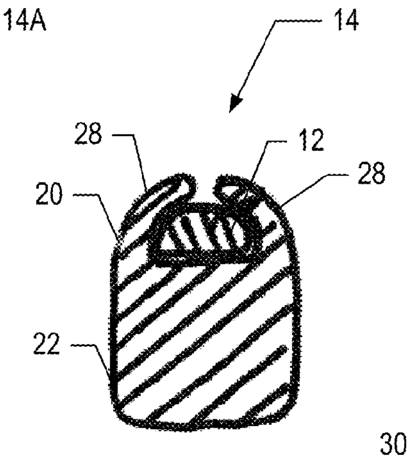
FIG. 10 is a cross-sectional view of another embodiment of the connector after the arms of the upper clamp portion have assumed the closed position around the thoracic sliding rod.

The sequence of closing the lower clamp arms 30 of the connector 14 is shown in FIGS. 7A and 7B. In FIG. 7A, the connector 14 is exposed to ambient or a lower temperature such that the lower clamp arms 30 remains in the open position; however, as shown in FIG. 7B, when the connector 14 is exposed to a temperature warmer than ambient temperature, for example 36.8 degrees centigrade, the properties of the shape-memory alloy cause the lower clamp arms 30 to bend such that lower conduit 34 is defined between arms 30. As shown in FIG. 8A, the elongated thoracic sliding rod 12 may be disposed within the upper conduit 32 of the connector 14 when the upper clamp arms 28 of the upper clamp portion 20 are in the open position during implantation of the sliding rod system 10 within the patient. After implantation, the core body temperature of the patient warms the connector 14 such that properties of the shape-memory cause the upper clamp arms 28 to assume the closed position and slidably engage the thoracic sliding rod 12 as illustrated in FIG. 8B.

After implantation of the sliding rod system 10 when the thoracic sliding rod 12 is secured to a plurality of ribs 46 by a series of connectors 14, the thoracic sliding rod 12 applies a continuous corrective force to the spinal column 48 by virtue of the fixed engagement of the connectors 14 to each respective rib 46. This is accomplished without impeding natural growth of the patient, thereby eliminating the need for subsequent growth-related surgical adjustments to the sliding rod system 10.

Referring back to FIG. 17, the single rod embodiment of the sliding rod system 10 is illustrated. In this embodiment, a pair of thoracic sliding rods 12A and 12B are implanted in the patient such that sliding rod 12A is engaged to the ribs 46 on the left side of the patient's rib cage and the sliding rod 12B is engaged to the ribs 46 on the right side of the patient's rib cage using various types of connectors 14. As set forth herein, the discussion of the thoracic sliding rod 12A and the various connectors 14 that connect the rod 12A to the left side of the patient's rib cage will also apply to the elongated rod 12B and the various connectors 14 that connect rod 12B to the right side of the patient's rib cage.

Figure 18:
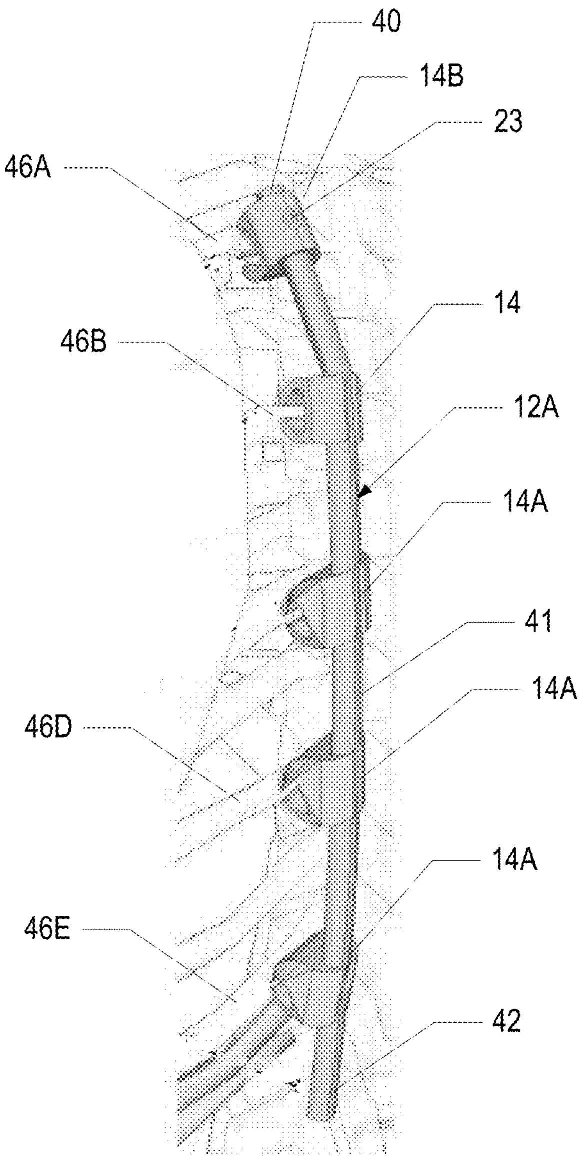
FIG. 18 is an isolated enlarged perspective view of the sliding rod system engaged to a plurality of ribs along one side of a patient's rib cage.

As shown in the enlarged view of FIG. 18, the thoracic sliding rod 12A is engaged to respective ribs 46 through various types of connectors 14 as shall be discussed in greater detail below. In one embodiment, the thoracic sliding rod 12A may have a semi-hemispherical cross-section having a body that defines an upper rod portion 40 at one end and a lower rod portion 42 at the opposite end thereof, although other embodiments may have other cross-sectional configurations, such as circular, rectangular and square. In one embodiment, the upper rod portion 42 of the thoracic sliding rod 12A is fixedly secured via a set screw 23 (FIGS. 19 and 20) to an anchor connector 14B along the upper portion of the patient's rib cage while the middle portion 41 of the sliding rod 12A is secured to remaining ribs 46 by either a regular connector 14 or an angled connector 14A.

Figure 12:
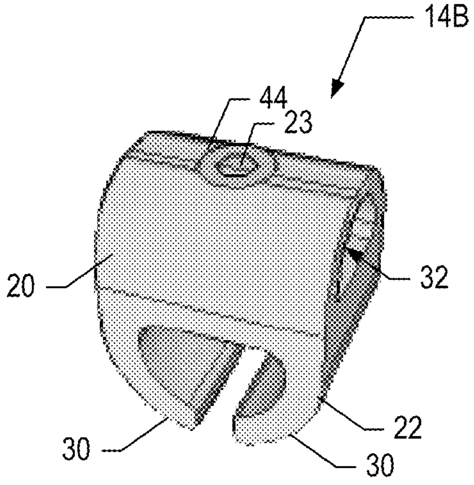
FIG. 12 is an elevated perspective view of an embodiment of the connector for anchoring the thoracic sliding rod.
Figure 19:
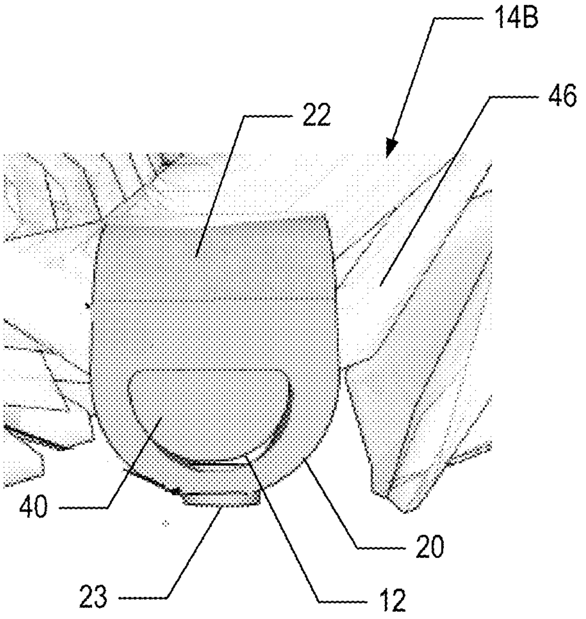
FIG. 19 is an enlarged perspective end view of the sliding rod system showing the connector anchoring the upper end of the thoracic sliding rod securing the connector to the sliding rod through the set screw.
Figure 20:
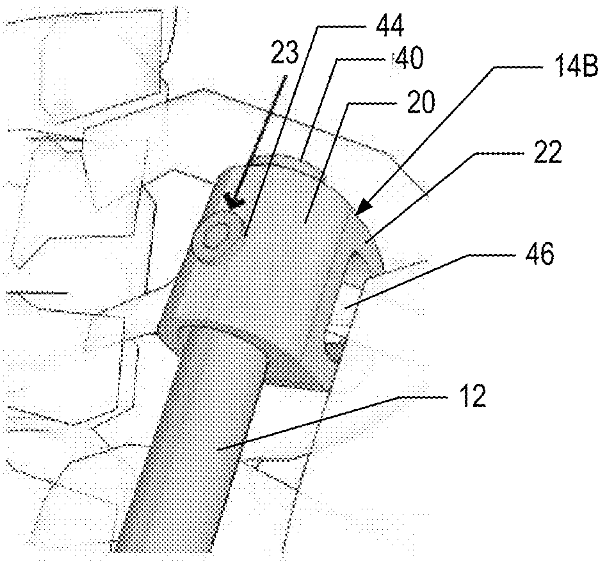
FIG. 20 is another enlarged perspective view of the sliding rod system showing the connector anchoring the upper end of the thoracic sliding rod.

Referring to FIGS. 12, 19 and 20, one type of connector 14, the anchor connector 14B, provides a means for securing the upper rod portion 40 of the thoracic sliding rod 12A to the anchor connector 14B. As such, the anchor connector 14B is the only connector 14 that prevents the thoracic sliding rod 12 to slide within the upper conduit 32 as the patient's rib cage expands during patient growth. The anchor connector 14B defines an aperture 44 in communication with upper conduit 32 that is adapted to receive a set screw 23 that engages the upper rod portion 40 of the thoracic sliding rod 12A in a manner that prevents movement of the rod 12A relative to the anchor connector 14B. The anchor connector 14B has a configuration similar to the regular connector 14 with lower clamp arms 30 adapted to assume a closed position around the ribs 46 at the warmer second temperature range; however, the upper clamp portion 20 of anchor connector 14B has a fully closed configuration and lacks the upper clamp arms 28 that would normally bend around the thoracic sliding rod 12A when the connector 14 assumes the closed position. As such, the thoracic sliding rod 12A is engaged to the anchor connector 14B by inserting sliding rod 12A through the upper conduit 32 when engaging the sliding rod 12A to the anchor connector 14B.

Figure 13:
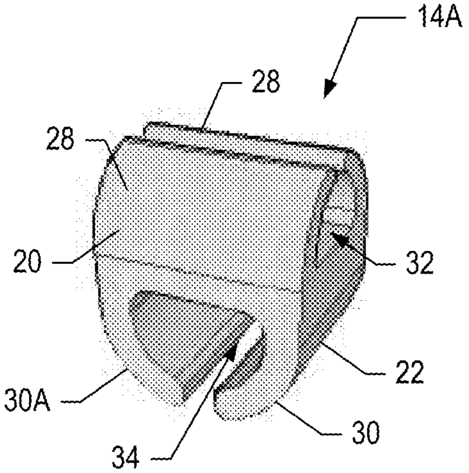
FIG. 13 is an elevated perspective view of an embodiment of the connector having a lower clamp portion with angled rib arms.

The sliding rod system 10 may further include a right-angled or left-angled connector 14A adapted for slidable engagement along multiple locations of the thoracic sliding rod 12A and 12B, respectively, as shown in FIG. 17. Referring to FIG. 13, the right-angled connector 14A, defines a similar upper clamp portion 20 that includes a pair of opposing upper clamp arms 28 that may assume a closed position around the thoracic sliding rod 12A when the correct temperature range is reached. However, the lower clamp portion 22 has a different configuration in that lower clamp arm 30A has a more gradually tapering and angled configuration relative to lower clamp arm 30. As such, lower clamp portion 22 is better adapted to engage particular ribs 46, especially those ribs 46 which have a more vertical orientation in relation to the spine. In general, the upper ribs 46 are more horizontal and are oriented to accept a regular anchor connector 14B or a regular sliding connector 14. In the distal part of the rib cage the ribs 46 assume a relatively more vertical orientation and may require an angled connector 14A. The angled connector 14A has a different orientation of the lower angled portion, depending on whether the connector 14A is implanted on the left or the right side of the rib cage. The left angled connector 14A has a similar configuration as the right angled connector 14B with the exception that the opposite lower clamp arm 30 is angled while the other lower clamp arm 30 has a normal configuration. In one embodiment, lower clamp arm 30A of either the right-angled and left-angled connectors 14A may have a 25 degree angle relative to the connector body A method of implanting the sliding rod system 10 is shown in FIGS. 17-20. This method of implantation of the sliding rod system 10 is illustrated with thoracic instrumentation such as would be used for an isolated thoracic scoliosis. Under general endotracheal anesthesia and continuous anesthesia monitoring as well as intraoperative spinal cord monitoring, the patient is first placed into a prone position on the spinal table (not shown). After the patient's back has been prepped and draped sterile, a midline skin incision is used and the back is exposed to the deep fascia. The trapezius muscle is then separated from its attachment on the spinous processes. Under the trapezius muscle, the surgeon identifies the longitudinal muscles overlying the ribs on either side of the spine. The medial aspect of the ribs are then exposed extraperiostally. Generally, alternating medial ribs are identified and exposed. For example, the thoracic scoliosis bilateral ribs #2, 4, 6, 8 and 10 may be exposed to accept the connectors 14 during implantation of the sliding rod system 10.

In one embodiment, the method for implanting the sliding rod system 10 includes engaging the anchor connector 14B to an upper rib 46, such as rib #2. The connector 14 is first chilled in a zero degree centigrade ice bath with the lower arms 30 of the connector 14 spread in an open position. The connector 14 is then placed onto the second rib with the lower arms 30 in the open position. As the lower arms 30 warm up to the body temperature of the patient, the arms 30 assume a closed position (FIG. 11) and securely fix the connector 14 to the rib. Additional sliding connectors 14 or 14A are then placed bilaterally on the lower ribs, typically ribs #4, 6, 8 and 10 using the same technique as for the anchored connector 14B to the rib #2. An elongated rod 12 is then cut to the appropriate length and contoured to have the proper coronal and sagittal shape prior to insertion into the connectors 14. The upper rod portion 40 of the contoured thoracic sliding rod 12A is then inserted through the upper conduit 21 of the anchor connector 14B.

Figure 21A:
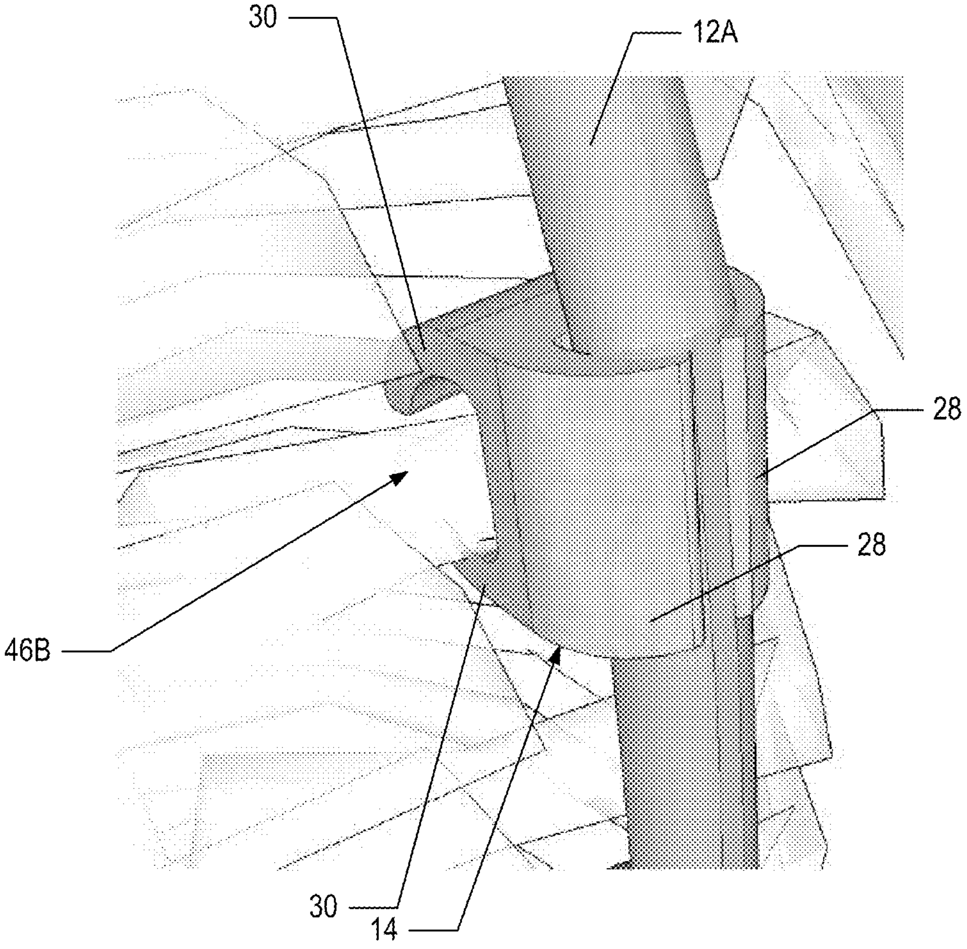
FIGS. 21A and 21B are enlarged perspective views of the regular sliding connector and angled connector, respectively, engaged along different portions of the thoracic sliding rod.
Figure 21B:
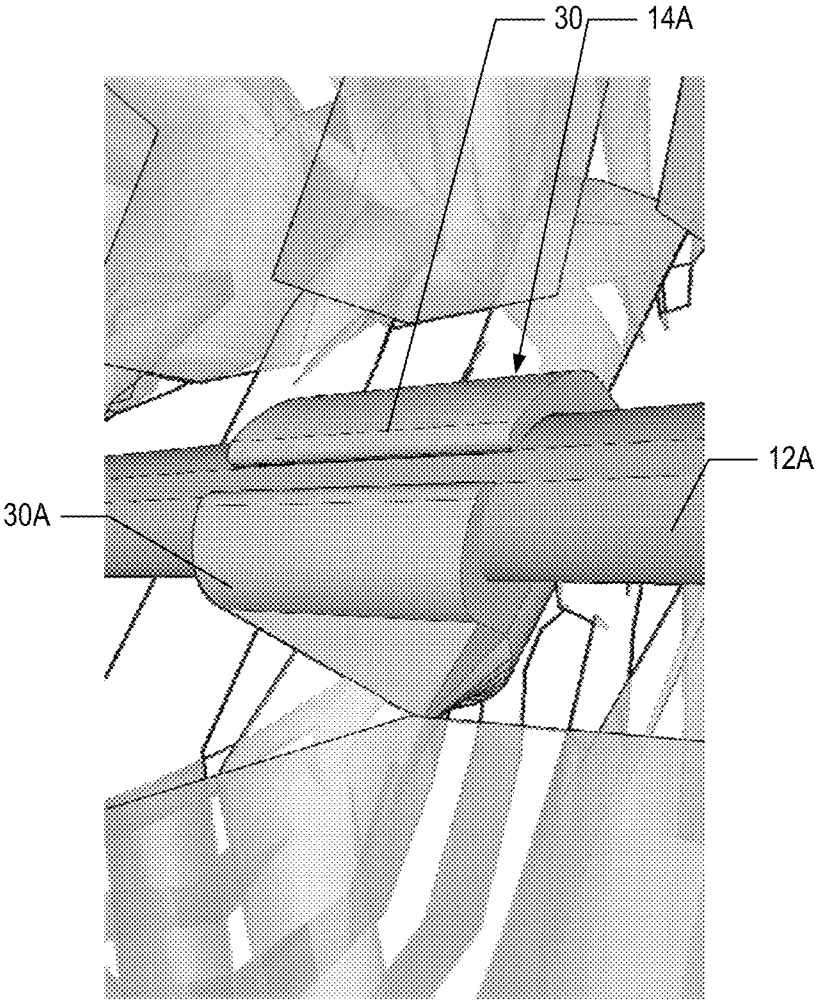

Once the anchor connector 14B is secured between the rib 46A and the thoracic sliding rod 12A, the sliding rod 12A is then inserted into the lower connectors 14, which are held in an open position to accept the thoracic rod 12A. In one embodiment shown in FIGS. 21A and 21B, a regular connector 14 may be engaged between rib 46B and sliding rod 12A (FIG. 21A), while right-angled connectors 14A may be engaged between respective ribs 46C, D and E and sliding rod 12A (FIG. 21B). As discussed above, the connectors 14 are in the open position during implantation of the sliding rod system 18 and will only assume the closed position around the ribs 46 or the thoracic sliding rod 12 until the correct surrounding temperature is reached by each respective connector 14, 14A or 14B.

Once implantation of the sliding rod system 10 is completed on one side of the rib cage, the surgeon then repeats the implantation procedure for the thoracic sliding rod 12B on the opposite side of the rib cage. Radiographs are obtained to confirm proper implant insertion position and deformity correction. The deep muscle tissue and skin are then closed in any fashion preferred by the surgeon. It should be noted that no post-operative bracing is usually required.

Figure 22A:
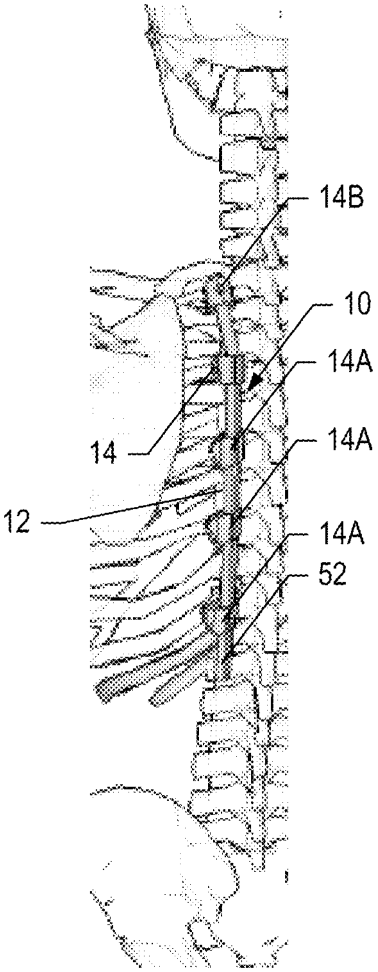
FIGS. 22A and 22B illustrate the sliding engagement of the thoracic sliding rod relative to the connectors in the single rod embodiment of the sliding rod system as a patient grows over time.
Figure 22B:
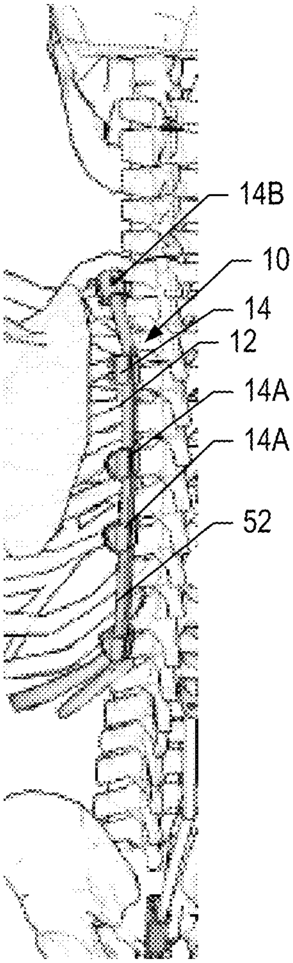

Once the implantation of the sliding rod system 10 is completed, the regular connectors 14 will gradually slide relative to the thoracic sliding rod 12 as the pediatric patient grows over time. FIGS. 22A and 22B illustrate the gradual slidable engagement of the connectors 14 relative to the thoracic sliding rod 12A from initial implantation (FIG. 22A) when the patient is about three years old through a two year period of time as the patient grows and the separation between the ribs 46 increases (FIG. 22B).

Figure 14:
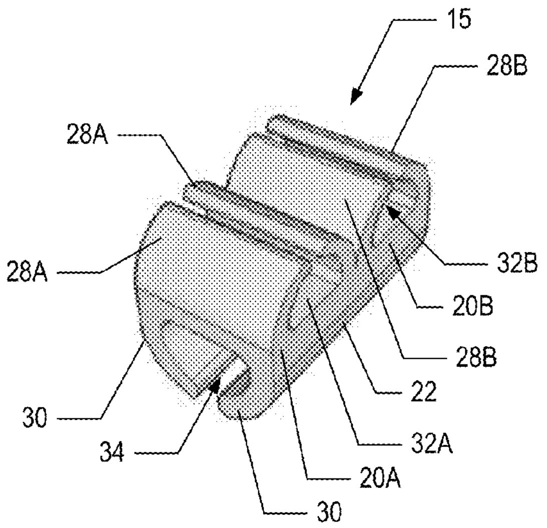
FIG. 14 is an elevated perspective view of an embodiment of the connector having an upper double rod clamp portion for sliding engagement with the thoracic sliding rods.
Figure 15:
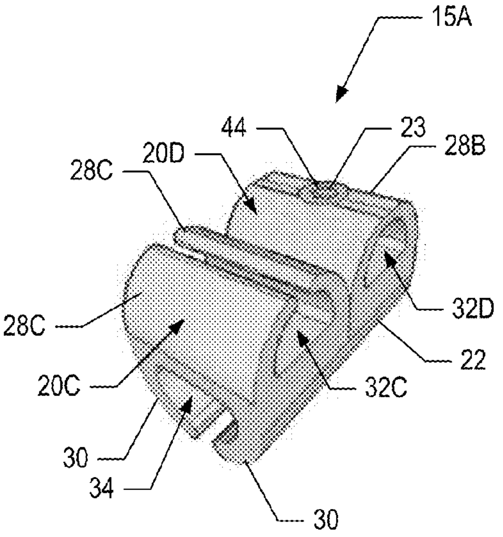
FIG. 15 is an elevated perspective view of yet another embodiment of the connector having an upper double rod clamp portion adapted to anchor one of the thoracic sliding rods.
Figure 16:
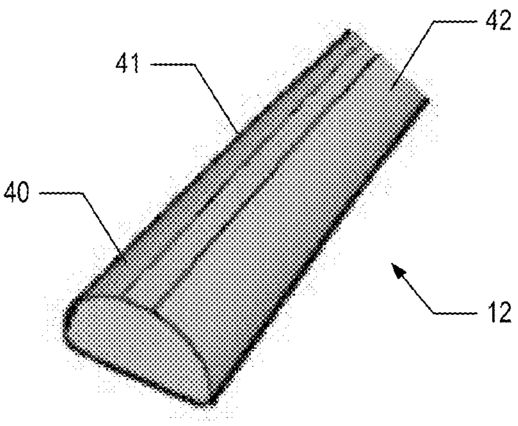
FIG. 16 is a perspective view of the thoracic sliding rod which is contoured to resist rotation of the connector about the sliding rod.
Figure 23:
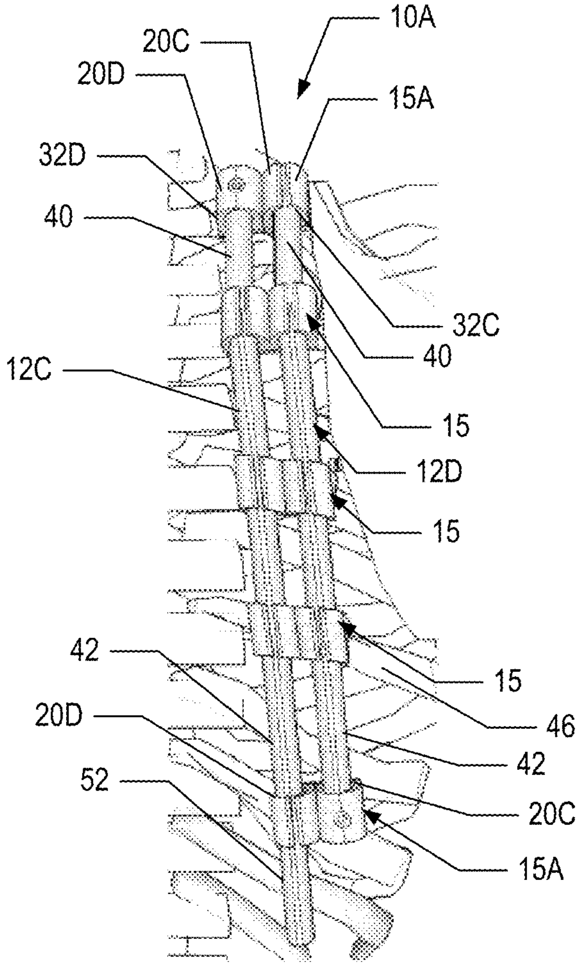
FIG. 23 is an elevated perspective view of the double rod embodiment of the sliding rod system engaged along the right side of a patient's rib cage.

Referring to FIGS. 14, 15 and 23, a double rod embodiment of the sliding rod system, designated 10A, is illustrated. In the double rod embodiment of the sliding rod system 10A, two thoracic sliding rods 12 are implanted on each side of the patient's rib cage for a total of four thoracic sliding rods 12 being implanted in the patient. Each pair of thoracic sliding rods 12 are coupled together by a plurality of double rod connectors 15 along the middle portion 41 of each thoracic sliding rod 12C and 12D, while a double rod anchor connector 15A secures one of the upper and lower rod portions 40 and 42 of the thoracic sliding rods 12C and 12D, respectively. As shown in FIG. 14, the double rod connector 15 may include a pair of upper clamp portions 20A and 20B defining respective opposing clamp arms 28A and 28B that form respective conduits 32A and 32B transversely positioned relative to a lower clamp portion 22 that defines a pair of opposing clamp arms 30 that form a single conduit 34. The upper clamp portions 20A and 20B are adapted for slidable engagement with respective thoracic sliding rods 12C and 12D, while the lower clamp portion 22 is adapted to fixedly engage a respective rib 46.

Referring to FIG. 15, each double rod anchor connector 15A may include a pair of upper clamp portions 20C and 20D that are transversely positioned relative to a lower clamp portion 22 defining a pair of opposing clamp arms 30 that define a single conduit 34. The upper clamp portion 20C defines a pair of opposing clamp arms 28C, which in the closed position, form an upper conduit 32C in communication with an upper clamp channel 36 adapted to slidably engage the thoracic sliding rod 12C, while the upper clamp portion 20D defines a closed upper conduit 32D in communication with a set screw 23 adapted to securely engage the other thoracic sliding rod 12D. The double rod connector 15 and the double rod anchor connector 15A may be made from the same shape-memory alloy discussed above that assumes a closed position after implantation when the patient's core body temperature raises the temperature surrounding the connectors 15 and 15A such that the arms 28A, 28B, 28C and 30 may be bent to the closed positions illustrated in FIGS. 14 and 15.

Referring back to FIG. 23, a method of implanting the sliding rod system 10A is illustrated. The surgeon may access the spine of the patient in the same manner as discussed above. A plurality of double rod connectors 15 and 15A may then be implanted bilaterally, typically at alternating ribs 46. With the connectors 15 and 15A in the open position, upper rod portion 40 of the thoracic sliding rod 12D is disposed within the upper clamp conduit 32D defined by the upper clamp portion 20D of the double rod anchor connector 15A. Once the thoracic sliding rod 12C is so inserted through upper clamp conduit 32D, the set screw 27 is rotated until a secure engagement is achieved between the sliding rod 12C and the upper clamp portion 20D of double rod anchor connector 15A. Once the double rod anchor connector 15A is engaged to the upper rod portions 40 of each thoracic sliding rod 12C and 12D as well as an upper rib 46 such that the upper clamp portions 20A and 20B of each respective connector 15 is slidably engaged along the middle portion 41 of each of the thoracic sliding rods 12C and 12D, while the lower clamp portion 22 is securely engaged to a respective rib 46 once the core body temperature of the patient causes the shape-memory alloy of the double rod connectors 15 to assume the closed position after implantation.

Once the plurality of double rod connectors 15 are implanted and securely engaged to the pair of thoracic sliding rods 12C and 12D as well as the ribs 46 of the patient, the other double rod anchor connector 15A may be implanted to one of the lower ribs 46 of the patient in the same manner as discussed above. In one embodiment, the thoracic sliding rod 12A may include a lower rod portion 42 that defines a lower terminal portion 52 that extends the length of the sliding rod 12C relative to the other sliding rod 12D. The lower terminal portion 52 of sliding rod 12C is disposed within the upper clamp portion 20C of the double rod anchor connector 15A such that a portion of the lower terminal portion 52 extends through the upper clamp portion 20C, while the lower rod portion 42 of the other thoracic sliding rod 12D is securely fixed to the upper clamp portion 20D. The terminal end portion 52 permits the thoracic sliding rod 12C to be continuously engaged to the double rod anchor connector 15A as the ribs 46 of the pediatric patient begin to separate over time from one another as the double rod anchor connector 15A slidably engages along the terminal end portion 52 of sliding rod 12C. After the thoracic sliding rods 12C and 12D are implanted, the other pair of thoracic sliding rods 12 are also similarly implanted on the opposite rib cage of the patient.

Figure 24A:
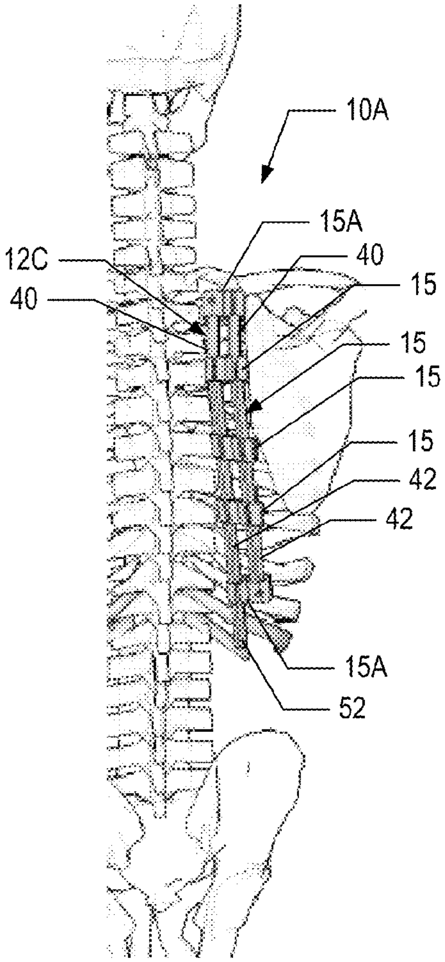
FIGS. 24A and 24B illustrate the sliding engagement of the thoracic sliding rods relative to the connectors in the double rod embodiment of the sliding rod system as a patient grows over time.
Figure 24B:
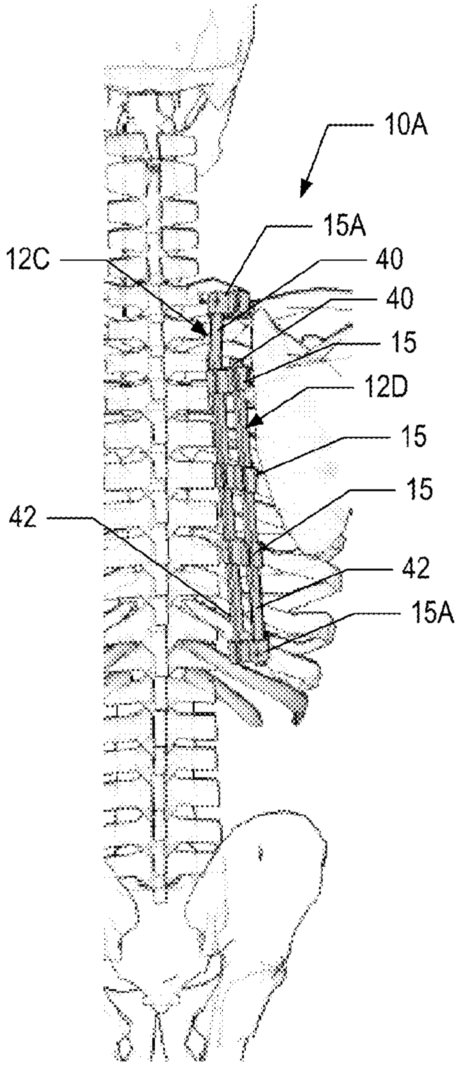

Referring to FIGS. 24A and 24B, the slidable engagement of the double rod embodiment of the sliding rod system 10A over time is illustrated. FIG. 24A illustrates the sliding rod system 10A after initial implantation in the pediatric patient at 3 years of age with the terminal end portion 52 of the thoracic sliding rod 12C extending through the double rod anchor connector 15A. Over a period of time as the patient grows, for example a two year period, the spine my grow by approximately 15% such that the distance between the adjacent connectors 15 and 15A begins to grow, as illustrated in FIG. 24B, thereby forcing the double rod anchor connector 15A to slide toward the end of the terminal end portion 52, while the upper rod portion 40 of the thoracic sliding rod 12D has become detached from the other double rod anchor connector 15A in order to accommodate the growing separation between the ribs 46.

Figure 25:
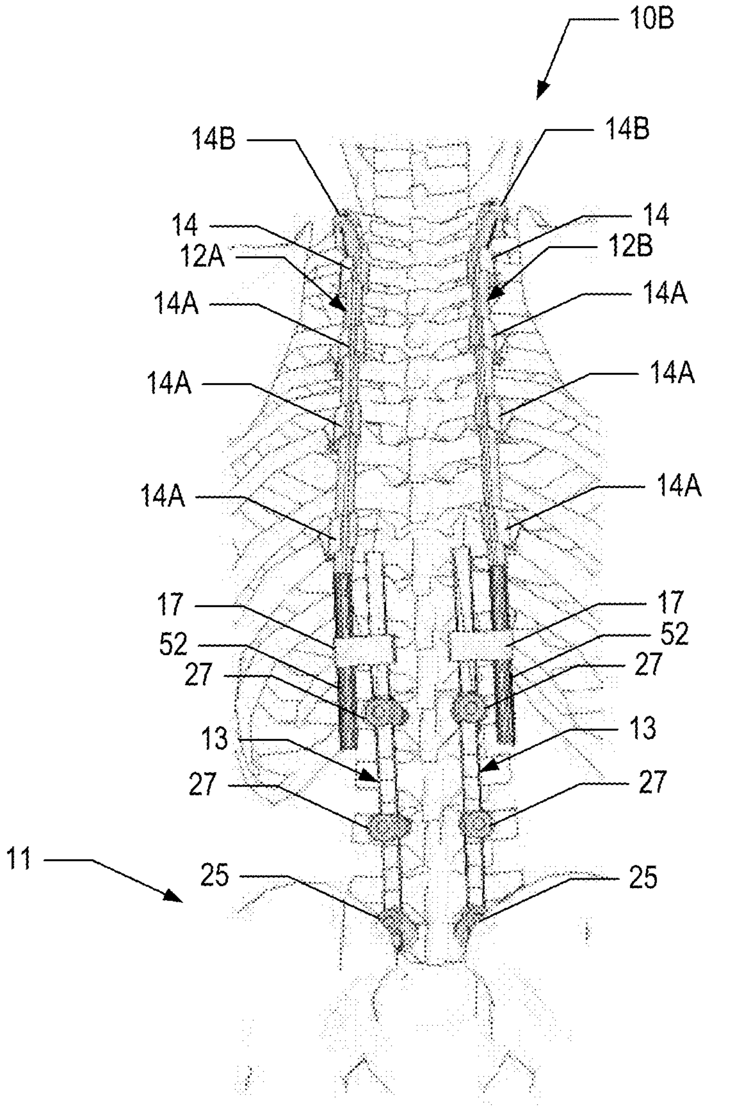
FIG. 25 is a perspective view of the single rod embodiment for the sliding rod system showing a sliding lumbar rod component.

Referring to FIG. 25, an embodiment of the sliding rod system, designated 10B, is shown with the lower portion of system 10B anchored to the patient's pelvis by a lumbar sliding rod component 11. The lumbar rod component 11 includes a pair of lumbar rods 13 that are operatively engaged to respective thoracic sliding rods 12A and 12B. In one embodiment, thoracic sliding rods 12A and 12B may be engaged to the respective lumbar rods 13 through a respective long sliding rod-rod connector 17 such that the thoracic sliding rods 12 and the lumbar sliding rods 13 are slidably engaged with respect to connector 17.

Figure 30:
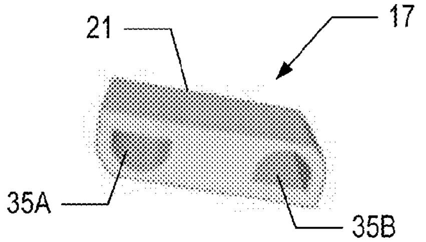
FIG. 30 is a perspective view of a long sliding rod-rod connector used with the sliding lumbar rod component.

As shown in FIG. 30, the long sliding rod-rod connector 17 includes a body 21 that defines a pair of opposing inverted conduits 35A and 35B with conduit 35A being adapted to slidably engage the thoracic sliding rod 12, while conduit 35B is adapted to slidably engage the lumbar sliding rod 13 in order to accommodate the increasing separation of the ribs 46 during patient growth. In another embodiment shown in FIG. 32, a shorter version of the long sliding rod-rod connector 17, designated 17A, is illustrated and may include a shorter body 21A that defines a similar pair of opposing inverted conduits 35A and 35B that are formed closer together than the same conduits 35A and 35B defined by the long sliding rod-rod connector 17. The short sliding rod-rod connector 17A is adapted to accommodate pediatric patients having smaller than normal skeletal structures.

Figure 29:
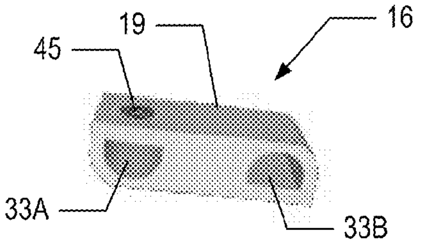
FIG. 29 is a perspective view of a long fixed rod-rod connector used with the sliding lumbar rod component.
Figure 31:
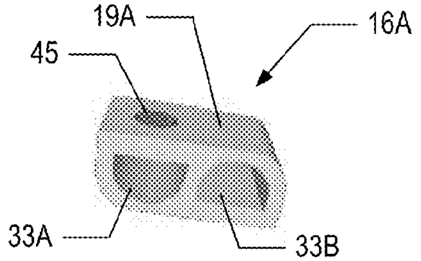
FIG. 31 is a perspective view of a short fixed rod-rod connector used with the sliding lumbar rod component.
Figure 32:
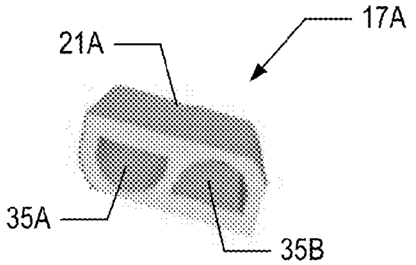
FIG. 32 is a simplified illustration of the short sliding rod-rod connector used with the sliding lumbar rod component.
Figure 33:
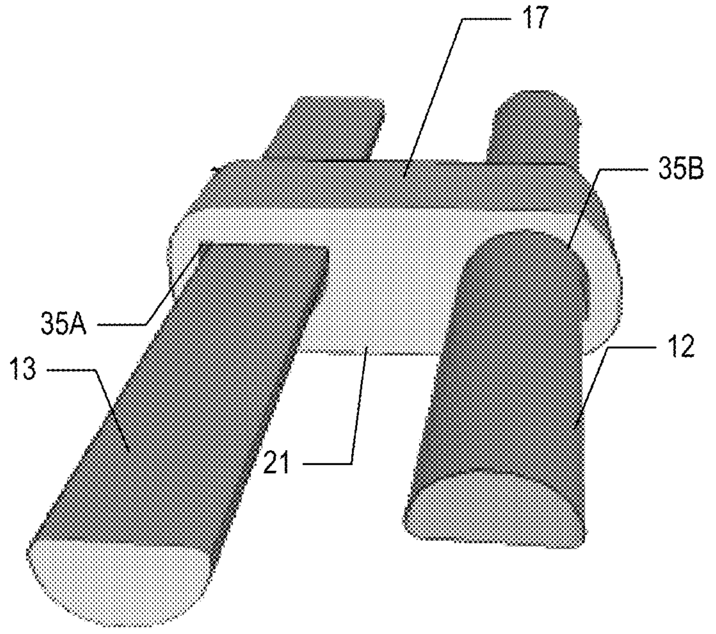
FIG. 33 is a simplified illustration of the long sliding rod-rod connector in sliding engagement with the lumbar sliding rod and the thoracic sliding rod, respectively.
Figure 34:
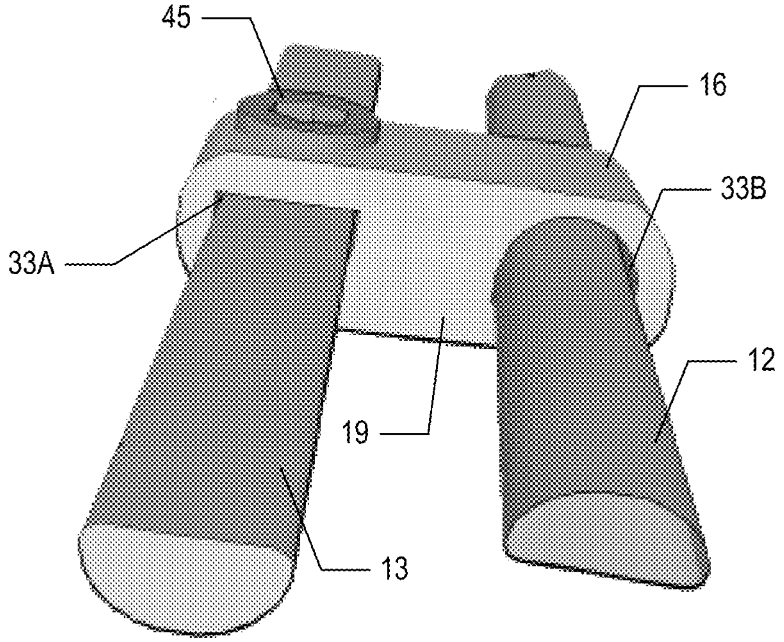
FIG. 34 is a perspective view showing the long fixed rod-rod connector fixedly engaged to the lumbar rod and in sliding engagement with the thoracic sliding rod.

Referring to FIG. 29, a long fixed rod-rod connector 16 is illustrated that may be used to engage the thoracic sliding rod 12 to the lumbar rod 13. The long fixed rod-rod connector 16 may include a body 19 that defines a pair of opposing inverted conduits 33A and 33B adapted to engage the thoracic sliding rod 12 and lumbar rod 13, respectively. In particular, the long fixed rod-rod connector 16 may be slidably engaged to the thoracic sliding rod 12 through conduit 33B, while being fixedly engaging to the lumbar rod 13 through conduit 33A as shown in FIG. 34. As such, the elongated rod 12 is permitted to slide relative to the connector 16 as the lumbar sliding rod 13 remains fixedly engaged to the long fixed rod-rod connector 16. The connector 16 further includes a set screw 45 in communication with conduit 33A that may be rotated into engagement with the lumbar sliding rod 13 so that the lumbar rod 13 is fixedly secured to the connector 16. In an alternative embodiment of the long fixed rod-rod connector 16, the short fixed rod-rod connector, designated 16A, is also adapted to slidably engage the thoracic sliding rod 12 and fixedly engage lumbar rod 13 as shown in FIG. 31. The short fixed rod-rod connector 16A includes a shorter body 19A that defines similar opposing inverted conduits 33A and 33B adapted to accommodate the smaller than normal skeletal structures of certain pediatric patients.

Figure 26:
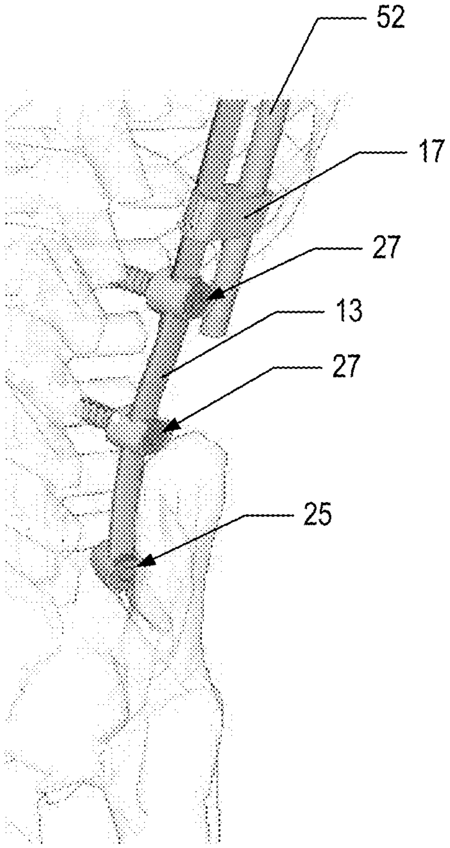
FIG. 26 is an isolated enlarged perspective view of the sliding lumbar rod component.
Figure 28:
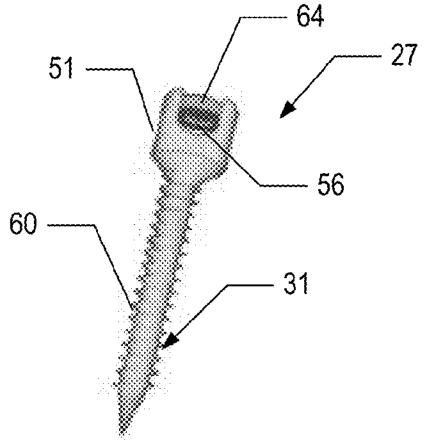
FIG. 28 is a perspective view of a fixed head screw having a sliding head portion used with the lumbar rod component.

As further shown in FIGS. 25 and 26, the lumbar rod component 11 includes a plurality of fixed head screws 27 that are in sliding engagement with the pair of lumbar sliding rods 13 to accommodate separation as the patient grows over time. Referring to FIG. 28, the fixed head screw 27 includes a body 31 that defines a head portion 51 in communication with a threaded lower portion 60 that is secured into the pedicle bone of a pediatric patient. The head portion 51 defines a conduit in communication with a rotatable nut 64 for capturing the thoracic sliding rod 13, but being a loose connection so that the thoracic sliding rod 13 is free to slide relative to the connectors 15. After implantation of the fixed head screws 27 into the lumbar pedicle, the lumbar sliding rod 13 is inserted into the conduit 56 and the rotatable nut 64 rotated by the surgeon until the rotatable nut 64 captures the thoracic sliding rod 13. The rotatable nut 64 and the conduit 56 are sized and shaped to permit the set screw 27 to capture the thoracic sliding rod 13 in a sliding engagement that permits the rod 13 to slide through the conduit 56 of the fixed head screw 27 as the pediatric patient grows and the plurality of ribs 46 begin to separate from one another over time.

Figure 27:
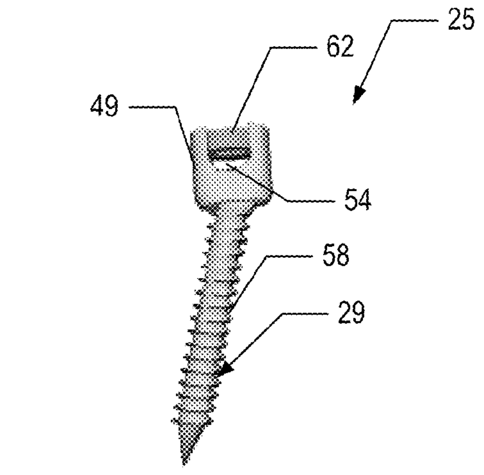
FIG. 27 is a perspective view of a polyaxial head screw having a non-sliding head portion used with the lumbar rod component.

As further shown in FIG. 27, the lumbar rod component 11 also includes a polyaxial head screw 25 that is adapted to anchor the lower portion of the thoracic sliding rod 13. A pair of polyaxial head screws 25 is in fixed engagement with respective lumbar sliding rods 13 to anchor the lower portion of the lumbar rod component 11 to the patient's lumbar or pelvic area. In addition, the polyaxial head screw 25 includes a head portion 49 for fixed engagement with the lumbar sliding rod 13 and a lower threaded portion 58 to secure polyaxial head screw 25 to either the lumbar pedicle of the patient or the pelvis through the iliac columns.

In one embodiment, the lower threaded portion 58 may be set at an angle relative to the head portion 49 such that the polyaxial head screw 25 is fixed to the lumbar pedicle or pelvis at an angle as illustrated in FIGS. 25 and 26. The head portion 49 of the polyaxial head screw 25 defines a conduit 54 sized and shaped to receive a rotatable set screw 62 that firmly secures the lumbar rod 13 to the head screw 25. The rotatable set screw 62 is thicker compared to the thinner set screw 64 and is used to secure the set screw 62 to the lowermost portion of the lumbar sliding rod 13 in order to firmly anchor the lumbar sliding rod 13 to the polyaxial head screw 25. During implantation of the lumbar rod component 11, the lumbar sliding rod 13 is inserted through the conduit 54 and the set screw 62 rotated into a fixed engagement with the sliding rod 13 such that the rod is anchored to the lumbar area of the patient. When the lumbar rod component 11 is implanted into the patient, the lower portion of the sliding rod system 10 is anchored to the patient's lumbar area such that the thoracic sliding rods 12 are allowed to slidably engage with the connectors 14 in order to accommodate the growing separation between the ribs 46 as the pediatric patient grows over time. In one aspect, the lumbar rod component 11 may be engaged to either the single rod embodiment 10 or the double rod embodiment 10A of the sliding rod system to provide an anchoring function. In addition, either the short or long version of the rod-rod connectors 16 or 17 may be used with the lumbar rod system 11 depending on the bone size of the patient, amount of spinal deformity, and the shape of the pediatric patient being accommodated.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method for correcting a spinal deformity in a patient comprising:

a) providing a sliding rod system comprising at least one thoracic sliding rod for slidable engagement with a plurality of connectors, each of the plurality of connectors having a connector body that includes an upper clamp portion transversely positioned relative to a lower clamp portion, the upper clamp portion including a pair of upper clamp arms that collectively define an upper conduit to engage the at least one thoracic sliding rod, and the lower clamp portion including a pair of opposing lower clamp arms that collectively define a lower conduit, wherein each connector body is made from a shape-memory alloy that permits the connector body to have an open position at a first temperature range while permitting the connector body to assume a closed position when exposed to a second temperature range that is warmer than the first temperature range;

b) surgically accessing a plurality of ribs of the patient and engaging at least one of the plurality of ribs to a respective connector such that each one the plurality of ribs engaged to a respective connector is disposed between the lower clamp arms of the respective connector in an open position, wherein the respective connector is exposed to a first temperature range;

c) inserting the at least one thoracic sliding rod through a respective connector such that the at least one thoracic sliding rod is disposed between the upper clamp arms of the respective one of the plurality of connectors in the open position, wherein the respective connector is exposed to the first temperature range; and d) allowing each of the plurality of connectors to assume the closed position when exposed to the second temperature range that is warmer than the first temperature range after engagement of the respective one of the plurality of connectors to the at least one thoracic sliding rod and the at least one of the plurality of ribs, wherein the at least one thoracic sliding rod remains slidably engaged with said connectors when said connectors are in the closed position and wherein said thoracic sliding rod applies a continuous corrective force to a spinal column of a patient.

2. The method of claim 1, wherein the continuous corrective force applied to the spinal column by the at least one thoracic sliding rod straightens the spinal column over time.

3. The method of claim 1, wherein the at least one of the plurality of connectors is an anchor connector, the anchor connector having an upper clamp portion defining an aperture for receiving a set screw, wherein the set screw is engaged to the at least one thoracic sliding rod for fixed engagement of the at least one thoracic sliding rod to the anchor connector.

4. A sliding rod system for correcting a spinal deformity in a pediatric patient comprising:

at least one thoracic sliding rod in slidable engagement with at least one connector with the at least one connector having a connector body that includes an upper clamp portion transversely positioned relative to a lower clamp portion the upper clamp portion including upper clamp arms that define an upper conduit to slidably engage the at least one thoracic sliding rod when in a closed position, and the lower clamp portion including lower clamp arms defining a lower clamp conduit to fixedly engage a respective rib of a patient;

a lumbar rod component comprising a rod-rod connector defining a pair of inverted conduits with one of the inverted conduits being adapted to be in slidable engagement with the at least one thoracic sliding rod while another one of the inverted conduits being adapted to be in slidable engagement with a lumbar sliding rod, said lumbar sliding rod and said thoracic sliding rod being substantially parallel to one another when each is engaged with a respective connector; said lumbar rod further comprising fixed head screws, each of the plurality of fixed head screws having a head portion and a threaded lower portion with the head portion defining a conduit in communication with a rotatable nut, wherein the lumbar sliding rod is adapted to be in slidable engagement between the rotatable nut and the conduit of the head portion of each of the plurality of fixed head screws;

wherein the at least one thoracic sliding rod applies a continuous corrective force to a spinal column of the patient through the fixed engagement of the at least one thoracic sliding rod with each respective rib of the patient as the at least one thoracic sliding rod is in slidable engagement with the at least one connector.

5. A sliding rod system for correcting a spinal deformity in a pediatric patient comprising:

at least one thoracic sliding rod in slidable engagement with at least one connector with the at least one connector having a connector body that includes an upper clamp portion transversely positioned relative to a lower clamp portion the upper clamp portion including upper clamp arms that define an upper conduit to slidably engage the at least one thoracic sliding rod when in a closed position, and the lower clamp portion including lower clamp arms defining a lower clamp conduit to fixedly engage a respective rib of a patient;

a lumbar rod component comprising a rod-rod connector defining a pair of inverted conduits with one of the inverted conduits being adapted to be in slidable engagement with the at least one thoracic sliding rod while another one of the inverted conduits being adapted to be in slidable engagement with a lumbar sliding rod, said lumbar sliding rod and said thoracic sliding rod being substantially parallel to one another when each is engaged with a respective connector, the lumbar rod component further comprising at least one head screw, the at least one head screw having a head portion and a threaded lower portion with the head portion defining a conduit in communication with a rotatable nut, wherein the lumbar sliding rod is adapted to be in fixed engagement between the rotatable nut and the conduit of the head portion of the at least one head screw;

wherein the at least one thoracic sliding rod applies a continuous corrective force to a spinal column of the patient through the fixed engagement of the at least one thoracic sliding rod with each respective rib of the patient as the at least one thoracic sliding rod is in slidable engagement with the at least one connector.

6. A sliding rod system for correcting a spinal deformity in a pediatric patient comprising:

at least one thoracic sliding rod in engagement with a plurality of connectors with each of the plurality of connectors having a connector body that includes an upper clamp portion transversely positioned relative to a lower clamp portion, the upper clamp portion consisting of a single pair of upper clamp arms that define an upper conduit to engage the at least one thoracic sliding rod when in a closed position, and the lower clamp portion including lower clamp arms defining a lower clamp conduit to fixedly engage a respective rib of a patient, said upper clamp arms and said lower clamp arms further including arm ends having a gap therebetween, each said gap being continuous with said corresponding conduit and having a diminished width in a closed position as compared to an open position;

wherein at least one of said plurality of connectors is fixed to the thoracic sliding rod in order to prevent sliding of the thoracic sliding rod within the upper conduit and at least one of the plurality of connectors is in slidable engagement with the thoracic sliding rod when in the closed position;

wherein the at least one thoracic sliding rod applies a continuous corrective force to a spinal column of the patient through the fixed engagement of the at least one thoracic sliding rod with each respective rib of the patient as the at least one thoracic sliding rod is in slidable engagement with the at least one of the plurality of connectors; and further comprising a lumbar rod component comprising a rod-rod connector defining a pair of inverted conduits with one of the inverted conduits being adapted to be in slidable engagement with the at least one thoracic sliding rod while another one of the inverted conduits being adapted to be in slidable engagement with a lumbar sliding rod, said lumbar sliding rod and said thoracic sliding rod being substantially parallel to one another when each is engaged with a respective connector.

7. The sliding rod system of claim 6, wherein the lumbar rod component further comprises a plurality of fixed head screws, each of the plurality of fixed head screws having a head portion and a threaded lower portion with the head portion defining a conduit in communication with a rotatable nut, wherein the lumbar sliding rod is adapted to be in slidable engagement between the rotatable nut and the conduit of the head portion of each of the plurality of fixed head screws.

8. The sliding rod system of claim 6, wherein the lumbar rod component further comprises at least one head screw, the at least one head screw having a head portion and a threaded lower portion with the head portion defining a conduit in communication with a rotatable nut, wherein the lumbar sliding rod is adapted to be in fixed engagement between the rotatable nut and the conduit of the head portion of the at least one head screw.

9. A sliding rod system for correcting a spinal deformity in a pediatric patient comprising:

at least one thoracic sliding rod in engagement with a plurality of connectors with each of the plurality of connectors having a connector body that includes an upper clamp portion transversely positioned relative to a lower clamp portion, the upper clamp portion consisting of a single pair of upper clamp arms that define an upper conduit to engage the at least one thoracic sliding rod when in a closed position, and the lower clamp portion including lower clamp arms defining a lower clamp conduit to fixedly engage a respective rib of a patient, said upper clamp arms and said lower clamp arms further including arm ends having a gap therebetween, each said gap being continuous with said corresponding conduit and having a diminished width in a closed position as compared to an open position;

wherein at least one of said plurality of connectors is fixed to the thoracic sliding rod in order to prevent sliding of the thoracic sliding rod within the upper conduit and at least one of the plurality of connectors is in slidable engagement with the thoracic sliding rod when in the closed position;

wherein the at least one thoracic sliding rod applies a continuous corrective force to a spinal column of the patient through the fixed engagement of the at least one thoracic sliding rod with each respective rib of the patient as the at least one thoracic sliding rod is in slidable engagement with the at least one of the plurality of connectors; and wherein the upper clamp portion of the at least one connector that is fixed to the thoracic sliding rod further defines an aperture for receiving a set screw for engagement against the at least one thoracic sliding rod and thereby prevent slidable engagement between the at least one connector and the at least one thoracic sliding rod.

10. A sliding rod system for correcting a spinal deformity in a pediatric patient comprising:

at least one thoracic sliding rod in engagement with a plurality of connectors with each of the plurality of connectors having a connector body that includes an upper clamp portion transversely positioned relative to a lower clamp portion, the upper clamp portion consisting of a single pair of upper clamp arms that define an upper conduit to engage the at least one thoracic sliding rod when in a closed position, and the lower clamp portion including lower clamp arms defining a lower clamp conduit to fixedly engage a respective rib of a patient, said upper clamp arms and said lower clamp arms further including arm ends having a gap therebetween, each said gap being continuous with said corresponding conduit and having a diminished width in a closed position as compared to an open position;

wherein at least one of said plurality of connectors is fixed to the thoracic sliding rod in order to prevent sliding of the thoracic sliding rod within the upper conduit and at least one of the plurality of connectors is in slidable engagement with the thoracic sliding rod when in the closed position;

wherein the at least one thoracic sliding rod applies a continuous corrective force to a spinal column of the patient through the fixed engagement of the at least one thoracic sliding rod with each respective rib of the patient as the at least one thoracic sliding rod is in slidable engagement with the at least one of the plurality of connectors;

wherein the connector body of the at least one connector includes a lower clamp portion defining opposing clamp arms that form a single conduit and a pair of upper clamp portions with each of the upper clamp portions defining opposing clamp arms that form respective conduits, wherein the lower clamp portion is transversely positioned relative to the pair of upper clamp portions; and wherein one of the pair of upper clamp portions of the at least one connector that is fixed to the thoracic sliding rod further defines an aperture for receiving a set screw for engagement against the at least one thoracic sliding rod and thereby prevent slidable engagement between the at least one connector and the at least one thoracic sliding rod.

11. A sliding rod system comprising:

a pair of thoracic sliding rods being engaged to a plurality of connectors adapted to be engaged to one or more ribs along one side of a patient's rib cage and another pair of thoracic sliding rods being engaged to another plurality of connectors adapted to be engaged to another one or more ribs along the other side of the patient's rib cage, each of said pair of thoracic sliding rods being in fixed engagement with at least one of said plurality of connectors and in slidable engagement with at least one of said plurality of connectors, such that a continuous corrective force is applied to the patient's spinal column by each pair of thoracic sliding rods, each of the plurality of connectors having a connector body that includes a pair of upper clamp portions transversely positioned relative to a lower clamp portion with each of the upper clamp portions consisting of a single pair of upper clamp arms that collectively define a respective upper conduit that is engaged to a respective one of the pair of thoracic sliding rods, and the lower clamp portion including opposing lower clamp arms that collectively define a lower conduit that is adapted to be fixedly engaged to a skeletal structure of the patient, wherein the connector body is made from a shape-memory alloy that permits each pair of upper clamp arms and the lower clamp arms of the connector body to have an open position at a first temperature range while permitting each pair of upper clamp arms and the lower clamp arms of the connector body to assume a closed position when exposed to a second temperature range that is warmer than the first temperature range such that at least one of the pair of upper clamp portions being slidably engaged with one of the pair of thoracic sliding rods and the lower clamp portion is adapted to being fixedly engaged to the skeletal structure of a patient, wherein one of the upper clamp portions of one of the plurality of connectors further defines an aperture that receives a set screw for fixed engagement with one of the pair of thoracic sliding rods.

* * * * *